(12) United States Patent
Ludurczak

(10) Patent No.: US 9,897,568 B2
(45) Date of Patent: Feb. 20, 2018

(54) NW-FET SENSOR COMPRISING AT LEAST TWO DISTINCT SEMICONDUCTING NANOWIRE DETECTORS

(71) Applicant: Commissariat A L'Energie Atomique et aux Energies Alternatives, Paris (FR)

(72) Inventor: Willy Ludurczak, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/387,878

(22) Filed: Dec. 22, 2016

(65) Prior Publication Data

US 2017/0184540 A1 Jun. 29, 2017

(30) Foreign Application Priority Data

Dec. 24, 2015 (FR) ...................... 15 63324

(51) Int. Cl.
*G01N 27/414* (2006.01)
*H01L 29/06* (2006.01)

(52) U.S. Cl.
CPC ..... *G01N 27/4146* (2013.01); *H01L 29/0673* (2013.01)

(58) Field of Classification Search
CPC .............. G01N 27/4146; G01N 27/414; H01L 29/06773; H01L 29/66575; H01L 29/66568
See application file for complete search history.

(56) References Cited

U.S. PATENT DOCUMENTS 9,318,573 B2 * 4/2016 Moon ............... H01L 29/66439
2004/0036126 A1 * 2/2004 Chau ...................... B82Y 10/00
257/401

(Continued)

FOREIGN PATENT DOCUMENTS

WO WO 2011/017077 A2 2/2011
WO WO 2011/154363 A2 12/2011
WO WO 2014/060894 A2 4/2014

OTHER PUBLICATIONS

Chen, G. et al. "Multi-VT Design of Vertical Channel Nanowire FET for Sub-10nm Technology Node" Nanoelectronics Conf. (INEC) 2016 IEEE Int. published online Oct. 13, 2016 pp. 1-2.*

(Continued)

*Primary Examiner* — Asok K Sarkar
*Assistant Examiner* — Grant Withers
(74) *Attorney, Agent, or Firm* — Oblon, McClelland, Maier & Neustadt, L.L.P.

(57) ABSTRACT

NW-FET sensor comprising:
  first and second semiconducting nanowires;
  a first semiconducting source portion, of which the first and second parts doped differently from each other are connected to the first ends of the nanowires;
  a second semiconducting drain portion, of which the first and second parts doped differently from each other are connected to the second ends of the nanowires;
  a first electrical contact placed on the first semiconducting portion and electrically connected to the first and second parts of the first semiconducting portion;
  a second electrical contact placed on the second semiconducting portion and electrically connected to the first and second parts of the second semiconducting portion;

14 Claims, 14 Drawing Sheets

(56) References Cited

U.S. PATENT DOCUMENTS

| | | | |
|---|---|---|---|
| 2005/0064185 A1* | 3/2005 | Buretea | B82Y 10/00 428/364 |
| 2005/0079659 A1* | 4/2005 | Duan | B82Y 10/00 438/197 |
| 2005/0181587 A1* | 8/2005 | Duan | B82Y 10/00 438/551 |
| 2006/0091481 A1* | 5/2006 | Li | B82Y 10/00 257/401 |
| 2007/0267625 A1* | 11/2007 | Wang | B82Y 10/00 257/14 |
| 2008/0061284 A1* | 3/2008 | Chu | B82Y 10/00 257/9 |
| 2008/0210987 A1* | 9/2008 | Bondavalli | B82Y 15/00 257/253 |
| 2008/0218740 A1* | 9/2008 | Williams | B82Y 20/00 356/72 |
| 2008/0237568 A1* | 10/2008 | Kobayashi | B82Y 10/00 257/9 |
| 2009/0321835 A1* | 12/2009 | Wirbeleit | H01L 27/11 257/365 |
| 2010/0044777 A1 | 2/2010 | Hong et al. | |
| 2011/0248698 A1* | 10/2011 | Kikuchi | G01N 27/4145 324/76.11 |
| 2013/0154016 A1* | 6/2013 | Glass | H01L 29/78 257/368 |
| 2013/0237039 A1* | 9/2013 | Sleight | H01L 21/02104 438/479 |
| 2015/0303289 A1* | 10/2015 | Lee | G01N 27/4146 257/24 |
| 2016/0003770 A1* | 1/2016 | Klootwijk | G01N 27/4146 73/31.06 |
| 2017/0038326 A1* | 2/2017 | Motayed | G01N 27/16 |
| 2017/0125526 A1* | 5/2017 | Hatem | H01L 29/155 |
| 2017/0154960 A1* | 6/2017 | Rachmady | H01L 29/0676 |
| 2017/0186846 A1* | 6/2017 | Badaroglu | H01L 29/42392 |

OTHER PUBLICATIONS

French Preliminary Search Report dated Sep. 23, 2016 in French Application 15 63324, filed on Dec. 24, 2015 (with English Translation of Categories of Cited Documents).

Perrine Batude et al. "3-D Sequential Integration: A Key Enabling Technology for Heterogeneous Co-Integration of New Function with CMOS", IEEE Journal on Emerging and Selected Topics in Circuits and Systems, vol. 2, No. 4, 2012, 9 pages.

R. Gaddi et al. "MEMS technology integrated in the CMOS back end", Microelectronics Reliability 50, 2010, 3 pages.

S.E. Naimi et al. "Temperature influence on Ph-ISFET sensor operating in weak and moderate inversion regime: Model and circuitry", Sensors and Actuators B 202, 2014, 9 pages.

* cited by examiner

NW-FET SENSOR COMPRISING AT LEAST TWO DISTINCT SEMICONDUCTING NANOWIRE DETECTORS

TECHNICAL DOMAIN AND PRIOR ART

The invention relates to the domain of NW-FET ("Nano-Wire Field Effect Transistor") sensors, the operating principle of which is similar to that of ISFET ("Ion Sensitive Field Effect Transistor") type sensors used particularly to detect electrically charged particles in a fluid, for example to make a pH meter.

ISFET type devices are used to detect a concentration of charges in a solution. This variation in the concentration of charges acts like a variation in the gate potential of such an FET device, thus modulating the channel current in a nanowire of the ISFET device.

FIG. 1 diagrammatically shows an ISFET type device 10. The device 10 comprises, on a dielectric layer 12 corresponding for example to the buried dielectric layer of an SOI substrate, a drain region 14, a source region 16 and a semiconducting nanowire, for example silicon, forming a channel 18 and extending between the drain and source regions 14, 16. A dielectric layer 20 is placed on the dielectric layer 12 and covers the source and drain regions 14, 16 and the channel 18. An opening 22 passes through the dielectric layer 20 and opens up on the channel 18. The opening 22 forms a microfluid cavity in which a fluid 24 is introduced. When an electric charge 26 present in the fluid 24 is located in the microfluid cavity, close to the channel 18, a variation of the current circulating in the channel 18 is then obtained by polarisation of the channel 18 when this electric charge moves and modifies the distance between the electric charge 26 and the channel 18. This current circulating in the channel 18 also varies when the number of charges present close to the channel 18 is modified.

Such devices can also be made collectively in the form of a detection matrix to increase the density of sensors per unit area. This is very advantageous in the case of detection of a single charge 26 carried by a particle in the solution 24, so as to increase the probability of detection of the charge by one of the sensors. In this case of the detection of a single particle, it is also necessary to address each sensor individually in the matrix formed, which is equivalent to being able to identify the sensor in which the channel current varies.

However, the density with which these devices can be made is limited, particularly due the dimensions of the drain and source regions 14, 16 that cannot be reduced below a certain value because these regions must be electrically connected through vias to address the devices individually. These vias are defined by openings made in the drain and source regions 14 and 16 above the lower metallic contact zones formed in a stack under the dielectric layer 12. This stack can be obtained after the SOI substrate is transferred (and then thinned) on the "Back-end of Line" type substrate of a CMOS circuit.

PRESENTATION OF THE INVENTION

Therefore there is a need to disclose a solution to improve the density at which electrical charges or electrically charge molecules can be detected, and also to propose a solution for improving the density of a matrix of NW-FET sensors in which the sensor within this matrix in which there is a variation of the channel current can be identified (sensor addressing function).

One embodiment discloses an NW-FET sensor for this purpose, comprising at least:

first and second semiconducting nanowires forming two distinct channels;

a first semiconducting portion forming a source region, of which a first part doped with a first type of conductivity (in other words an acceptor or donor type doping) is connected to a first end of the first semiconducting nanowire, and a second end of which doped with a second type of conductivity opposite the first type of conductivity (in other words an acceptor doping if the first part is a donor type doping, or a donor doping if the first part is an acceptor type doping) is connected to a first end of the second semiconducting nanowire;

a second semiconducting portion forming a drain region, of which a first part doped with the first type of conductivity is connected to a second end of the first semiconducting nanowire, and a second end of which doped with the second type of conductivity is connected to a second end of the second semiconducting nanowire;

a first electrical contact placed on the first semiconducting portion and electrically connected to the first and second parts of the first semiconducting portion;

a second electrical contact placed on the second semiconducting portion and electrically connected to the first and second parts of the second semiconducting portion;

In such a sensor, the first and second semiconducting nanowires form two detectors associated with the same source and drain regions. These two detectors can be addressed individually from each other due to the different doping of the different parts of the semiconducting portions forming the source and drain regions. Due to sharing of the source and drain regions by the two detectors formed, the area occupied by these two detectors is equivalent to the area occupied by a single sensor according to prior art forming a single detector because this area is dictated by the dimensions of the source and drain regions. Thus, the density at which electrical charges or electrically charged molecules can be detected by such sensors is much than the density that can be obtained by sensors according to prior art.

The differentiation or addressing made between the first and second semiconducting nanowires is achieved by opposite doping of the semiconducting parts forming their drain and source regions and the fact that single pole transport of charges with opposite natures takes place in each channel thus formed. Thus, transport in the channel associated with drain and source regions with donor type doping, or N doping (denoted NW-N), is preponderantly by electron type carriers (negative charge carrier in a semiconductor). Transport in the channel associated with drain and source regions with acceptor type doping, or P doping (denoted NW-P), is preponderantly by hole type carriers (positive charge carrier in a semiconductor).

In the same way as the polarisation conditions of a MOSFET transistor, a difference of potentials between the drain and source regions (Vds) can modify the current in the channel of each detector. In the disclosed sensor, if a positive voltage Vds is applied (which means that a potential applied on the drain is higher than the potential applied on the source), the majority electrons in the NW-N detector channel tend to displace from the source to the drain, and majority holes in the channel of the NW-P detector also tend to displace from the source to the drain. Depending on the conventions, two currents are formed in opposite directions (the current being in the same direction as holes and the opposite direction to electrons) in the two channels of the sensor and therefore potentially a very small total current passing through the structure (under specific polarisation conditions).

Unlike a conventional MOSFET transistor in which a gate potential Vgs is applied to define the static operation of the transistor, the gate potential in this case is defined by the charges present close to one or more channels or by the position of a single charge above one of the channels. Thus, if a negative charge approaches the channel of the NW-P type detector and under the Vds conditions described above, this movement of the charge tends to increase the majority holes current described above, while the majority electrons current in the NW-N type detector is less affected or is not affected at all. This modifies the global current passing through the structure, in other words the global current in the two channels of the sensor. It is possible to use this principle to identify which nanowire detected displacement of a charge, depending on the nature of the variation of the global current and knowing the polarity of this charge. A distinction can thus be made between the following cases (using the conventions mentioned above):

when a negative charge approaches the NW-P detector, the channel current in the NW-P detector increases and the global current decreases;

when a negative charge approaches the NW-N detector, the channel current in the NW-N detector decreases and the global current increases;

when a positive charge approaches the NW-P detector, the channel current in the NW-P detector decreases and the global current increases;

when a positive charge approaches the NW-N detector, the channel current in the NW-N detector increases and the global current decreases;

Such a sensor is advantageously used in the framework of a sequential 3D co-integration of sensors on a CMOS control and read circuit, and in which nanowires in the sensors are addressed individually by the CMOS circuit both by independent connections between sensors with two semiconducting nanowires as described above and by a physical differentiation within source and drain regions obtained due to different doping in the first and second parts of the source and drain regions to which the nanowires are connected.

The first and second semiconducting nanowires and the first and second semiconducting portions can be parts of a single continuous semiconducting element. The expression "single continuous semiconducting element" refers to a semiconductor portion not interrupted by a vacuum or by another material, in other words forming a single semiconducting part.

The first part of the first semiconducting portion can be separated from the second part of the first semiconducting portion by a distance equal to at least about 20 nm or equal to at least about 250 nm and/or the first part of the second semiconducting portion can be separated from the second part of the second semiconducting portion by a distance equal to at least about 20 nm or equal to at least about 250 nm.

The NW-FET sensor may be such that:

the semiconductor of the first and second nanowires is intrinsic (forming a sensor with intrinsic channels), or the first semiconducting nanowire is doped with a first type of conductivity with a doping level less than the doping level of the first parts of the first and second semiconducting portions, and the second semiconducting nanowire is doped with a second type of conductivity with a doping level less than the doping level of the second parts of the first and second semiconducting portions, or the first semiconducting nanowire is doped with the second type of conductivity and the second semiconducting nanowire is doped with the first type of conductivity.

A specific doping of the channels of the NW-N and NW-P nanowires may be applied in order to maximise the sensitivity of the sensor, in other words to maximise the global current variation under the effect of the displacement of an electric charge close to one of the sensor channels: if the channel of the NW-P detector is doped as P type, forming a P+/P/P+ type assembly with the source and drain regions, in other words such that the drain and source regions (P+ doping) are doped more than the channel (P doping), the detector has a much higher current than a device with an undoped channel.

Similarly, such a current increase is obtained in the channel of the NW-N detector comprising a (source+drain+channel) assembly doped with an N+/N/N+ type.

By adjusting the different N+/N/N+ and P+/P/P+ doping levels of channels of NW-N and NW-P detectors respectively and remaining within low Vds polarisation conditions, a structure can be obtained with a low global current in the presence of a non-zero Vds and with no applied gate potential.

The configuration in which the first and second nanowires are doped with the same type of conductivity as the source and drain regions associated with them has the advantage of increasing the current level circulating in the sensor when there is no applied gate potential, in other words increasing the intensity of the detection signal output by the sensor.

The NW-FET sensor can also comprise at least one first dielectric layer on which the semiconducting nanowires and the first and second semiconducting portions are placed.

In this case, the NW-FET sensor may also comprise at least one gate electrode placed in the first dielectric layer, facing at least one of the first and second semiconducting nanowires. With such a gate, the sensor can be polarised through the application of an electrical polarisation potential on the gate, at an operating point optimised for the sensitivity/noise ratio.

The NW-FET sensor may also comprise:

a substrate located under the first dielectric layer and comprising a CMOS control and read circuit;

electrical interconnection levels located in the first dielectric layer and electrically connected to the CMOS control and read circuit (levels forming a "Back-End-Of-Line" (BEOL) part);

at least two electrically conducting vias each passing through one of the first and second semiconductor portions and a part of the first dielectric layer, and electrically connecting the first and second electrical contacts to one of the electrical interconnection levels.

Another embodiment applies to a detection device comprising several NW-FET sensors like those described above, in which each of the NW-FET sensors or groups of NW-FET sensors are arranged adjacent to each other forming a detection matrix.

In each group of NW-FET sensors, one of the first and second semiconducting portions of a first of the NW-FET sensors in said group may be common to at least one second of the NW-FET sensors in said group and may comprise at least one third part doped with the first type of conductivity connected to one of the first and second ends of the first semiconducting nanowire of the second NW-FET sensor in said group, and a fourth part doped with the second type of conductivity connected to one of the first and second ends of the second semiconducting nanowire of the second NW-FET sensor in said group. In such a configuration, two sensors share one of their source and drain regions, which can further increase the detection density that can be achieved compared with sensors according to prior art. These two sensors can be seen as being connected to each other in series.

Each group of NW-FET sensors may comprise four first NW-FET sensors and eight second NW-FET sensors such that one of the first and the second semiconducting portions of the first NW-FET sensors is in common and the other of the first and second semiconducting portions of each is in common with two of the other second NW-FET sensors and such that one of the first and second semiconducting portions of each of the second NW-FET sensors is in common with another of the second NW-FET sensors. This configuration further optimises the space occupied by twelve NW-FET sensors and further improves the detection density that can be obtained.

A method of making an NWFET sensor is also disclosed, comprising steps to:
dope first regions of a semiconducting layer with a first type of conductivity, and second regions of the semiconducting layer with a second type of conductivity opposite the first type of conductivity;
etch the semiconducting layer, forming:
first and second semiconducting nanowires forming two distinct channels of the NW-FET sensor;
a first semiconducting portion forming a source region of the NW-FET sensor, of which a first part included in one of the first doped regions is connected to a first end of the first semiconducting nanowire, and a second part included in one of the second doped regions is connected to a first end of the second semiconducting nanowire;
a second semiconducting portion forming a drain region of the NW-FET sensor, of which a first part included in another of the first doped regions is connected to a second end of the first semiconducting nanowire, and a second part included in another of the second doped regions is connected to a second end of the second semiconducting nanowire;
make a first electrical contact on the first semiconducting portion and electrically connected to the first and second parts of the first semiconducting portion (for example formed by a metallic deposit that partially covers the first and second doped parts of the first semiconducting portion);
make a second electrical contact on the second semiconducting portion and electrically connected to the first and second parts of the second semiconducting portion (for example formed by a metallic deposit that partially covers the first and second doped parts of the second semiconducting portion);

The method may also include the implementation of steps before the doping step of the first and second semiconducting regions, to:
make a substrate comprising a CMOS control and read circuit;
make electrical interconnection levels in a first dielectric layer arranged on the substrate, the electrical interconnection levels being electrically connected to the CMOS control and read circuit;
make the semiconducting layer on the first dielectric layer, for example after the transfer of an SOI substrate onto the CMOS substrate formed and thinning of the stack thus obtained.

The method may also comprise application of a step, after the step to etch the semiconducting layer, to make at least two openings each passing through one of the first and second semiconducting portions and a part of the first dielectric layer and such that they open up on one of the levels of electrical interconnections, and then a step to deposit an electrically conducting material in the two openings and on the first and the second semiconducting portions, forming the first and second electrical contacts and two electrically conducting vias each passing through one of the first and second semiconducting portions and a part of the first dielectric layer, and electrically connecting the first and second electrical contacts to said one of the electrical interconnection levels.

BRIEF DESCRIPTION OF THE DRAWINGS

This invention will be better understood after reading the description of example embodiments given purely for information and in no way limitative with reference to the appended drawings on which.

Identical, similar or equivalent parts of the different figures described below have the same numeric references to facilitate the comparison between different figures.

The different parts shown on the figures are not necessarily all at the same scale, to make the figures more easily understandable.

The different possibilities (variants and embodiments) must be understood as not being mutually exclusive and can be combined with each other.

DETAILED PRESENTATION OF PARTICULAR EMBODIMENTS

Figure 1:
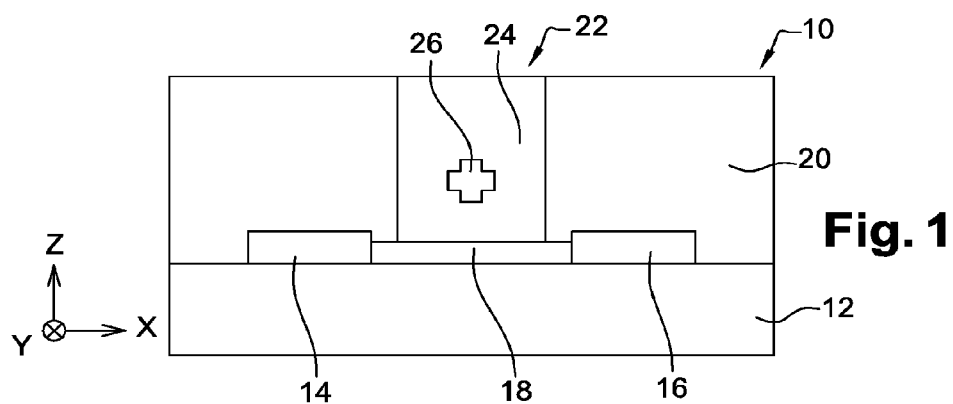
FIG. 1 shows an ISFET type device according to prior art.
Figure 2:
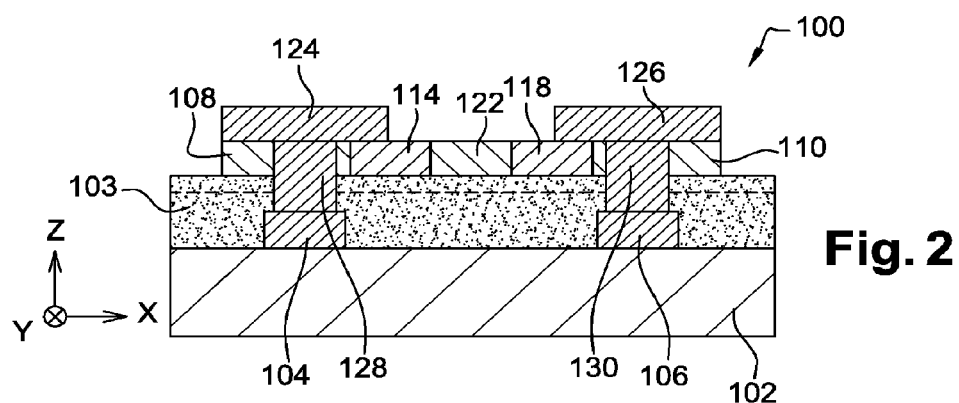
FIGS. 2 and 3 show a sectional side view and a top view respectively of a first embodiment of an NW-FET sensor.
Figure 3:
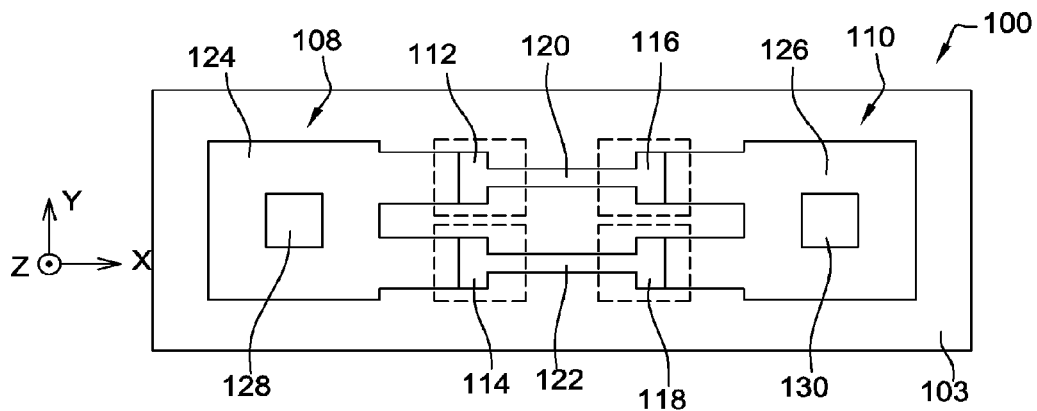

Refer firstly to FIG. 2 that shows a side sectional view of a first embodiment of an NW-FET sensor 100, and to FIG. 3 that shows a top view of the sensor 100.

The sensor 100 comprises a substrate 102 forming a CMOS back-end part electrically connected to the active part of the sensor 100, in which a CMOS read and control circuit is made, but is not shown in FIGS. 2 and 3. A first dielectric layer 103 is arranged on the substrate 102 and corresponds to the ILD (Inter-Layer Dielectric) layers between which electrical interconnection levels are made, also not shown on FIGS. 2 et 3, electrically connecting the CMOS read and control circuit to the active part of the sensor 100 (and to other sensors similar to the sensor 100, not shown on FIGS. 2 and 3 and also made on the same substrate 102). The last level of electrical interconnections (the level located closest to the active part of the sensor 100, or the level located furthest from the substrate 102) comprises connection pads electrically connected to the active part of the sensor 100 through conducting vias passing particularly through a part of the first dielectric layer 103. Two connection pads 104, 106 of the last electrical interconnections level are shown on FIGS. 2 and 3.

The sensor 100 comprises an active semiconducting part, for example comprising silicon, placed on the substrate 102 and comprising a first portion 108 forming a source region, and a second portion 110 forming a drain region of the sensor 100. A first part 112 of the first portion 108 is doped with a first type of conductivity, in this case P type, and a second part 114 of the first portion 108 is doped with a second type of conductivity opposite the first type of conductivity, in this case N type. The two parts 112, 114 are for example spaced from each other by a distance of at least 20 nm, or at least about 250 nm, so that opposite dopings made in the two parts 112, 114 can be clearly differentiated and are not superposed. Similarly, a first part 116 of the second portion 110 is doped with the first type of conductivity (P type), and a second part 118 of the second portion 110 is doped with the second type of conductivity (type N). The two parts 116, 118 are at a spacing from each other, like parts 112, 114.

FIG. 3 and the following figures symbolically show doped parts 112, 114, 116 and 118 each symbolically surrounded by a rectangle box shown in dashed lines to clearly identify these doped parts of portions 108, 110 from other undoped parts of these portions 108, 110. These boxes represent the initially doped regions in the semiconducting layer that was used to make portions 108, 110.

The active part of the sensor 100 also comprises two nanowires 120, 122 at a spacing from each other and forming two distinct channels of the sensor 100. A first end of the first nanowire 120 is connected to the first part 112 of the first portion 108 and a second end of the first nanowire 120 is connected to the first part 116 of the second portion 110. Moreover, a first end of the second nanowire 122 is connected to the second part 114 of the first portion 108 and a second end of the second nanowire 122 is connected to the second part 118 of the second portion 110. The nanowires 120, 122 thus form distinct channels but are connected to source and drain regions common to these two channels. Dopings and activation annealings are done before an ILD deposition.

A first electrical contact 124, in this case metallic, is placed on the first portion 108 and forms an electric contact common to the first and second parts 112, 114 of the first portion 108. A second electrical contact 126, also of the metallic type, is placed on the second portion 110 and forms an electric contact common to the first and second parts 116, 118 of the second portion 110. The first electrical connection 124 is electrically connected to the connection pad 104 through a first conducting via 128 passing through the first portion 108 and a part of the first dielectric layer 103 located between the connection pad 104 and the first portion 108. The second electrical connection 126 is electrically connected to the connection pad 106 through a second conducting via 130 passing through the second portion 110 and a part of the first dielectric layer 103 located between the connection pad 106 and the second portion 110.

Although the electrical contacts 124, 126 are common to the two detectors formed by the two nanowires 120, 122, these two detectors can be addressed individually due to the different dopings of the parts 112, 114, 116, 118 of the portions 108, 110 to which the nanowires 120, 122 are connected.

The electrical operating principle of the sensor 100 is as follows. When a positive or negative non-zero Vds polarisation voltage is applied between portions 108 and 110, a current circulates in the two detectors of the sensor 100. When the parts 112, 116 are P doped and the parts 114, 118 are N doped, electrons circulate predominantly in the nanowire 122 and holes circulate predominantly in the nanowire 120. When Vds>0, electrons and holes move from portion 108 (the source) towards portion 110 (the drain). When Vds<0, electrons and holes move from portion 110 towards portion 108.

Therefore, regardless of whether Vds is positive or negative, the global current circulating in the sensor 100 is zero if the numbers of carriers per unit time transiting in the nanowires 120, 122 (which takes account particularly of concentrations and mobility of charge carriers) are identical in parts 112, 114, 116, 118. When an electrical charge moves or is detected above one of the two nanowires 120, 122, this global current becomes non-zero or has a detectable variation because one of the currents of electrons or holes is modified. This current is read by the CMOS control and read circuit that is electrically connected to the detectors through electrical contacts 124, 126, conducting vias 128, 130 and electrical interconnection levels connecting these vias to the CMOS control and read circuit.

Therefore with such a sensor 100 allows the formation of, while occupying the same or a very similar semiconducting area as that occupied by the device 10 according to prior art described above (since the critical dimensions of the sensor 100 and the device 10 are the dimensions of the portions 108, 110), two detectors that operate independently of each other and for which the activity of a charge on one of the two nanowires can be identified by the variation of the global current in the structure and the polarity of the charge. Therefore, integration of such sensors 100 into a detection matrix containing several of these sensors 100 can increase the density of the detectors present on this matrix, because the device 10 according to prior art only forms a single detector for the entire area occupied by the device 10, while the sensor 100 forms two distinct devices.

Figure 4:
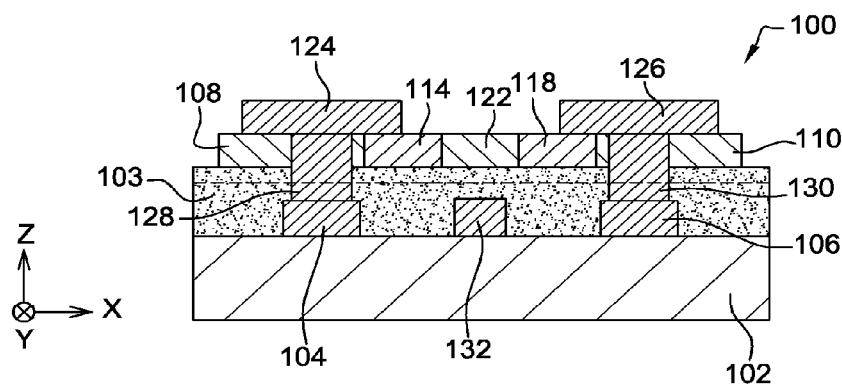
FIGS. 4 and 5 show a sectional side view and a top view respectively of a second embodiment of an NW-FET sensor.
Figure 5:
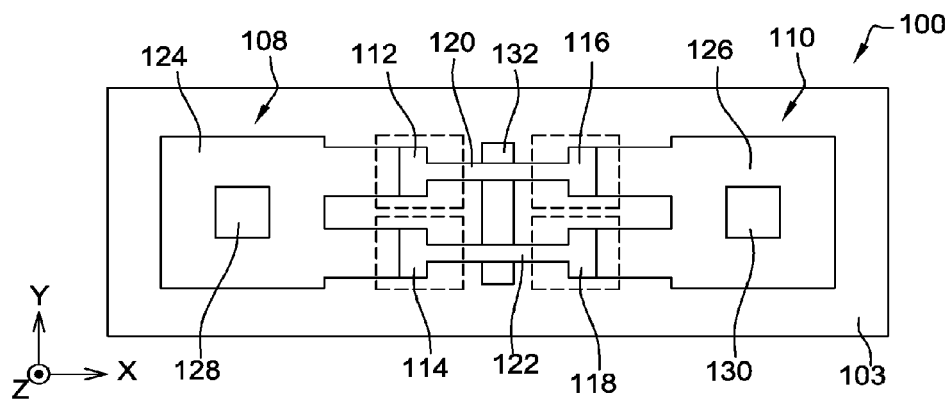

FIGS. 4 and 5 show a sectional side view and a top view respectively of a second embodiment of the NW-FET sensor 100.

Unlike the sensor 100 described above with reference to FIGS. 2 and 3, the sensor 100 according to this second embodiment also comprises an additional metallic portion 132 forming part of the last level of electrical interconnections and used as a gate electrode for the two detectors formed by the sensor 100. This metallic 132 portion is electrically connected to the CMOS control and read circuit that generates an electrical field in the nanowires 120, 122 when a gate potential is applied to this portion 132, so that the detectors containing the nanowires 120, 122 can be polarised at a required operating point or polarisation point. By judiciously choosing this operating point, the sensor 100 can be made to operate such that its sensitivity/noise ratio is improved (the sensitivity of the sensor relates to the value of its transconductance).

On the example in FIGS. 4 and 5, the portion 132 is common to the two nanowires 120, 122. As a variant, two metallic portions can be made side by side, each under one of the nanowires 120, 122, so that the two detectors of the sensor 100 can be polarised differently. According to another variant, it is possible that the portion 132 is placed facing only one of the two nanowires 120, 122, and in this case only one of the detectors of the sensor 100 can be preponderantly polarised due to the portion 132.

In the two embodiments described above, the nanowires 120, 122 of the sensors 100 comprise the intrinsic semiconductor. According to a first variant that can be applied to either of the embodiments described above, it is possible that the semiconductor of these nanowires 120, 122 is doped with the same type as the semiconducting parts, forming the source and drain regions to which the nanowires are connected. For example, considering the first embodiment of the sensor 100 shown on FIGS. 2 and 3, it is possible that the first nanowire 120 that is connected to the P doped parts 112, 116 is also formed from a P doped semiconductor, and that the second nanowire 122 that is connected to the N doped parts 114, 118 is also formed from an N doped semiconductor. In this case, the doping level of parts 112, 114, 116, 118 is higher than the doping level of nanowires 120, 122 (for example with the P doped nanowire 120 and P+ doped parts 112, 116, and the N doped nanowire 122 and the N+ doped parts 114, 118). This first variant is advantageous because it provides optimum sensitivity without any gate polarisation other than that of the charge to be detected, while assuring a very low current Id and therefore low consumption. The principle is based on the fact that the two nanowires 120, 122 have maximum transconductance at Vgs=0.

In other cases, the nanowires 120, 122 have transconductances for non-zero Vgs values and are polarised to improve the sensitivity of the detector.

According to a second variant, the semiconductor in the nanowires 120, 122 can be doped with the type opposite to the type with which the semiconductor of the semiconducting parts 112, 114, 116, 118 is doped. For example, considering the sensor 100 according to the first embodiment shown on FIGS. 2 and 3, it is possible that the first nanowire 120 that is connected to the P doped parts 112, 116 is formed from an N doped semiconductor and that the second nanowire 122 that is connected to the N doped parts 114, 118 is formed from a P doped semiconductor.

The advantage of these first and second variants is that the required polarisation point can be adapted depending on the sensitivity and the noise generated by the structure.

Regardless of which embodiment or variant is considered, several sensors 100 are advantageously made on the same substrate 102 and are placed adjacent to each other forming a detection matrix of a detection device 200.

The density with which the sensors 100 can be integrated into a detection matrix can be further increased by making the sensors 100 such that one of the two portions 108, 110 is common to one or several other sensors 100 of the device 200.

Figure 6:
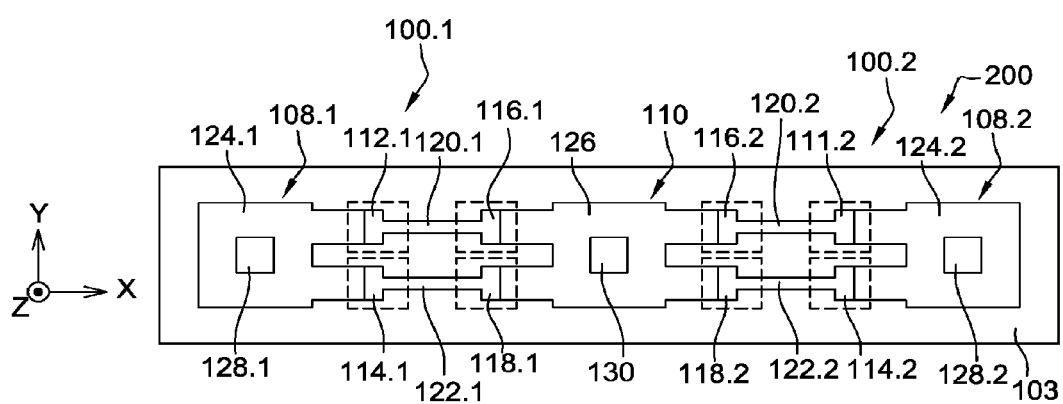
FIG. 6 shows a top view of a first embodiment of a detection device comprising NW-FET sensors with a common semiconducting portion.

FIG. 6 shows a top view of a first embodiment of such a detection device 200 comprising several sensors 100 forming a detection matrix. Only two of the sensors, references 100.1 and 100.2, of the device 200 are shown on FIG. 6. In this first embodiment of the detection device 200, the sensors 100 form two groups of sensors 100 sharing their second portion 110. On FIG. 6, the second portion 110 is common to the two sensors 100.1 and 100.2 and forms a drain region common to these two sensors 100.1 and 100.2.

The first sensor 100.1 comprises the same elements as the sensor 100 described above with reference to FIGS. 2 and 3, in other words a first semiconducting portion 108.1 including first and second parts 112.1 and 114.1 doped differently to each other, a second semiconducting portion 110 comprising first and second parts 116.1 and 118.1 doped differently from each other, first and second nanowires 120.1 and 122.1 the ends of which are connected to parts 112.1, 114.1, 116.1 and 118.1, electrical contracts 124.1 and 126 located on the portions 108.1 and 110, conducting vias 128.1 and 130 and the other elements of the back-end part of the sensor 100.

However, unlike the second portion 110 of the sensor 100 described above with reference to FIGS. 2 and 3, the second portion 110 shown on FIG. 6 also comprises a third part 116.2 doped with the first type of conductivity and a fourth part 118.2 doped with the second type of conductivity, in addition to the first and second parts 116.1, 118.1. These third and fourth parts 116.2, 118.2 are at a spacing from each other in the same way as the first and second parts 116.1, 118.1. The second electrical contact 126 is placed on these four parts 116.1, 118.1, 116.2 and 118.2 of the second portion 110 and therefore forms an electrical contact common to the first, second, third and fourth parts 116.1, 118.1, 116.2, 118.2 of the second portion 110.

The second sensor 100.2 also comprises a first semiconducting portion 108.2 that comprises a first part 112.2 doped with the first type of conductivity and a second part 114.2 doped with the second type of conductivity, these two parts 112.2, 114.2 being at a spacing from each other in a similar manner to parts 112.1 and 114.1 of portion 108.1.

The second sensor 100.2 also comprises a first nanowire 120.2 and a second nanowire 122.2 forming two distinct channels of the second sensor 100.2. A first end of the first nanowire 120.2 is connected to the third part 116.2 of the second portion 110 and a second end of the first nanowire 120.2 is connected to the first part 112.2 of the first portion 108.2 of the second sensor 100.2. A first end of the second nanowire 120.2 is connected to the fourth part 118.2 of the second portion 110 and a second end of the second nanowire 120.2 is connected to the second part 114.2 of the first portion 108.2 of the second sensor 100.2.

Finally, the first portion 108.2 of the second sensor 100.2 is covered by an electrical contact 124.2 forming an electrical contact common to the first and second parts 112.2, 114.2 of the portion 108.2. This electrical contact 124.2 is electrically connected to an additional connection pad formed in the last electrical interconnections level through a conducting via 128.2 passing through this first portion 108.2 and a part of the first dielectric layer 103 located between this additional connection pad and this first portion 108.2.

The four detectors formed by these two sensors 100.1 and 100.2 can be addressed individually due to the different dopings of the parts 112, 114, 116, 118 to which the nanowires 120, 122 of each of the sensors 100.1, 100.2 are connected, even though the second region 110 forms a drain region common to these four detectors (since polarisation of one of the sensors 100.1, 100.2 can be chosen depending on the source region on which the polarisation voltage is applied).

As a variant of the first embodiment of the device 200 previously described with reference to FIG. 6, it is possible that the doping types of the different parts of the semiconducting regions of the second sensor 100.2 are inverted from those described above, in other words the parts 116.2 and 112.2 of the second sensor 100.2 are doped with the second type of conductivity and the parts 118.2 and 114.2 of the second sensor 100.2 are doped with the first type of conductivity.

In the configuration shown on FIG. 6, the two sensors 100.1 and 100.2 are arranged to be in parallel with each other, in other words such that the nanowires 120, 122 of the two sensors 100.1, 100.2 have their large dimensions approximately along the same direction. As a variant, the two sensors 100.1 and 100.2 can be arranged differently relative to each other. For example, it is possible that the sensors 100.1 and 100.2 are arranged approximately perpendicularly to each other, in other words the largest dimensions of the nanowires 120.1, 122.1 of the first sensor 100.1 are oriented approximately perpendicular to the nanowires 120.2, 122.2 of the second sensor 100.2 (the nanowires 120, 122 of the two sensors being in the same plane). In this case, in the second portion 110, the third and fourth parts 116.2 and 118.8 at the portion 110 may be located on a side adjacent to the side on which the first and second parts 116.1, 118.1 are located, rather than on a side opposite to the side on which the first and second parts 116.1, 118.1 are located.

Furthermore, in the configuration shown on FIG. 6, the sensors 100 of the device 200 form groups of two sensors connected to each other in series and sharing the same portion of semiconductor forming a source or drain region of these sensors. As a variant, the sensors 100 can form groups of more than two sensors sharing their semiconducting portion in pairs.

Figure 7:
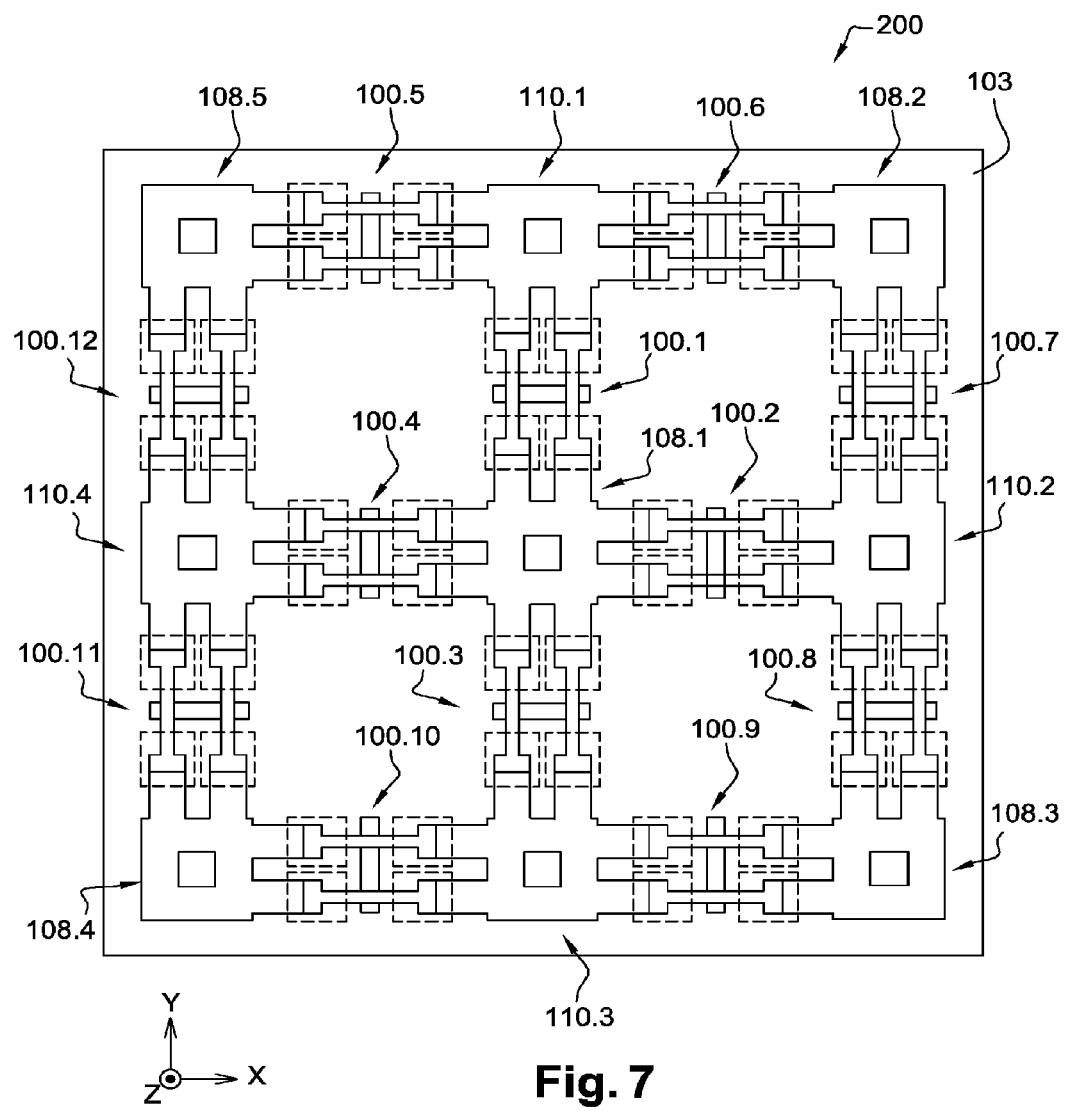
FIG. 7 shows a top view of a second embodiment of a detection device comprising NW-FET sensors with common semiconducting portions.
Figure 8:
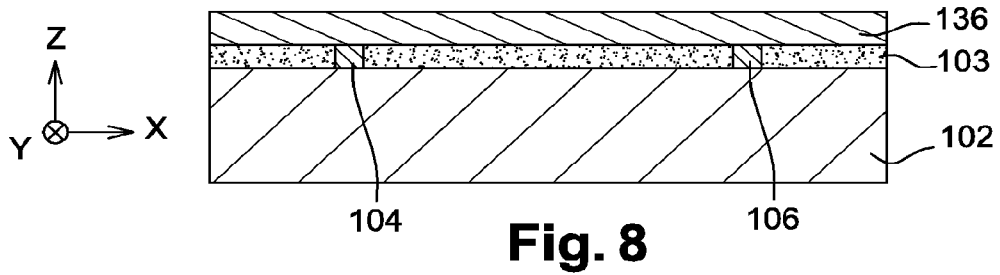
FIGS. 8 to 36 show steps in a method of making an NW-FET sensor according to a particular embodiment.
Figure 9:
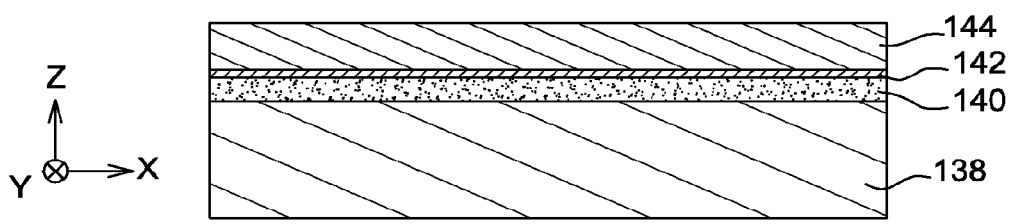

FIG. 7 is a top view of a second embodiment of a detection device 200 comprising a set of sensors 100 each forming two detectors that can be addressed independently, and each comprising semiconducting portions common to one, two or three other sensors 100.

Thus, in the configuration shown on FIG. 7, the device 200 comprises four first sensors 100.1, 100.2, 100.3 and 100.4 with a common first semiconducting portion 108.1. Therefore this first portion 108.1 comprising eight differently doped parts in pairs to which the nanowires of the four first sensors 100.1 to 100.4 are connected. The device 200 also comprises eight second sensors 100.5 to 100.12. Each of the second semiconducting portions 110.1, 110.2, 110.3 and 110.4 of the first four sensors 100.1 to 100.4 is common to two of the second sensors 100.5 to 100.12. Therefore each of the second portions 110.1 to 110.4 comprises six parts differently doped in pairs to which the nanowires of one of the four first sensors 100.1 to 100.4 and two of the eight sensors 100.5 to 100.12 sensors are connected. Thus on FIG. 7, the second portion 110.1 of the first sensor 100.1 is common to the second sensors 100.5 and 100.6, the second portion 110.2 of the first sensor 100.2 is common to the second sensors 100.7 and 100.8, the second portion 110.3 of the first sensor 100.3 is common to the second sensors 100.9 and 100.10, and the second portion 110.4 of the first sensor 100.4 is common to the second sensors 100.11 and 100.12. Finally, each of the second sensors 100.5 to 100.12 comprises a first semiconducting portion 108.2, 108.3, 108.4 or 108.5 common to another of the second sensors 100.5 to 100.12. Thus on FIG. 7, the first portion 108.2 is common to the second sensors 100.6 and 100.7, the first portion 108.3 is common to the second sensors 100.8 and 100.9, the first portion 108.4 is common to the second sensors 100.10 and 100.11, and the first portion 108.5 is common to the second sensors 100.12 and 100.5.

The second embodiment of the device 200 shown on FIG. 7 is particularly advantageous due to the high detection density that can be obtained with the twelve sensors 100.1 to 100.12 thus made, due to the fact the that the first and second semiconducting regions 108, 110 of these sensors are put in common. This principle can be extended to a larger matrix comprising a larger number of sensors.

The device 200 as described previously with reference to FIGS. 6 and 7 can be made from sensors 100 corresponding to any one of the previously described embodiments or variants of the sensor 100.

We will now describe an example embodiment of a method for making a sensor 100 with reference to FIGS. 8 to 36.

The CMOS Back-End part of the sensor 100 is made firstly in the substrate 102, in other words the CMOS transistors of the control and read circuit, and the level(s) of electrical interconnections made in the first dielectric layer 103 located on the substrate 102. Only the two connection pads 104, 106 of the last electrical interconnections level are shown on FIG. 8. The first dielectric layer 103 and the connection pads 104, 106 are covered with a first bonding layer 136, for example comprising silicon oxide deposited by a TEOS precursor.

At the same time as the CMOS Back-End of the sensor 100 is being made, another substrate is prepared so that a semiconducting layer that will used to make the active part of the sensor 100 can be transferred onto the substrate 102. On FIG. 9, this other substrate corresponds to an SOI substrate comprising a solid semiconducting layer 138, a buried dielectric layer 140 and a surface semiconducting layer 142 that in this case corresponds to a thin layer of silicon, less than about 10 µm thick. The surface layer 142 is covered with a second bonding layer 144, for example comprising silicon oxide deposited by a TEOS precursor.

Figure 10:
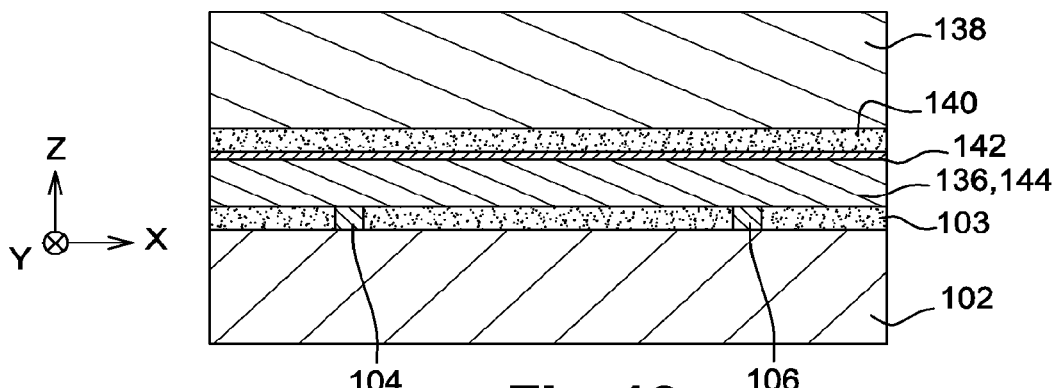
Figure 11:
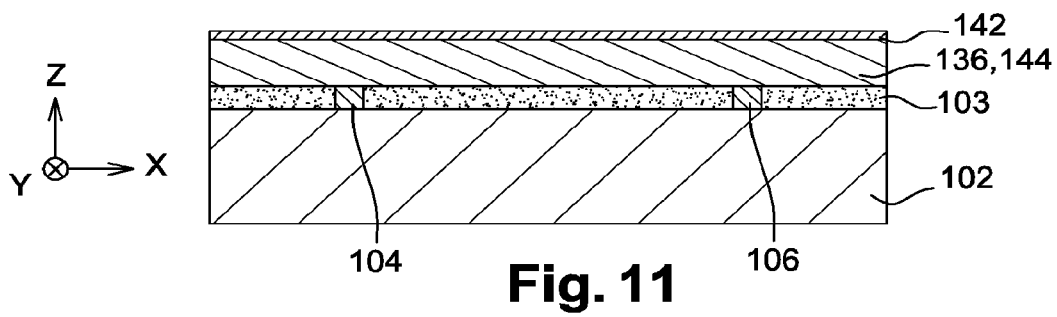

As shown on FIG. 10, the two previously made substrates are assembled to each other through their bonding layers 136, 144 fixed to each other for example by direct bonding.

The assembly obtained is then thinned by grinding and then by dry etching, eliminating the solid layer 138 and the buried dielectric layer 140, thus exposing the surface semiconducting layer 142. As a variant, it is possible that part of the thickness of the buried dielectric layer 140 can be kept to act as a hard mask later.

Figure 13:
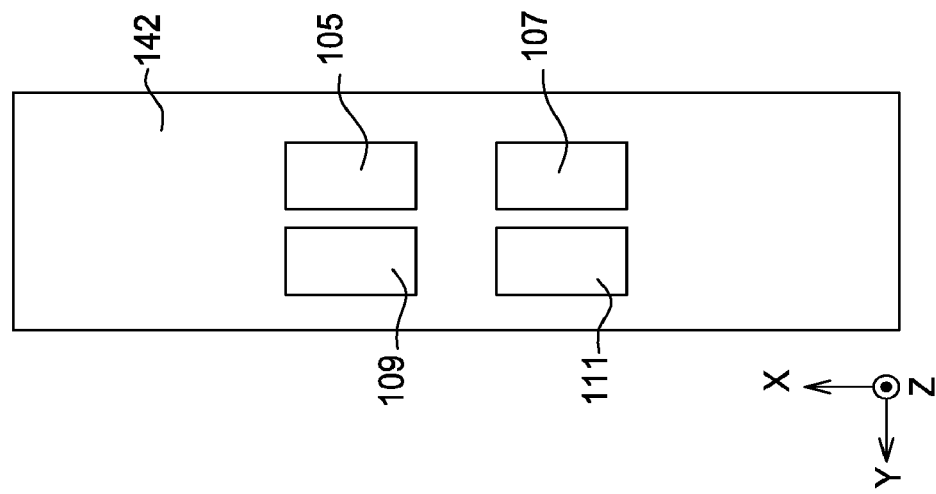
Figure 12:
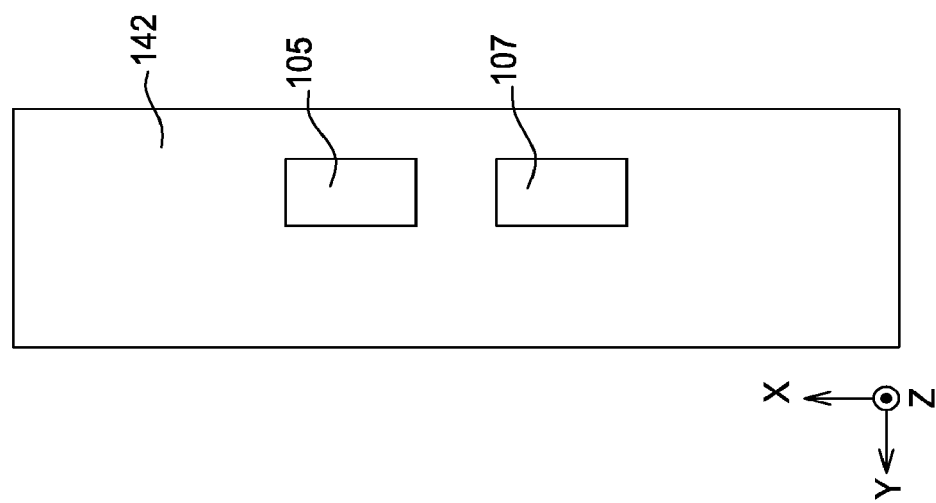

As shown on FIG. 12 that is a top view of the surface layer 142, a first step in the implantation of dopants according to the first type of conductivity is made in the first regions 105 and 107 of the layer 142 each including one of the future first parts 112 and 116 of the first and second semiconducting portions 108, 110 of the sensor 100. FIG. 13 shows that a second implantation of dopants with the second type of conductivity is made in the second regions 109 and 111 of the layer 142 each including one of the future second parts 114 and 118 of the first and second semiconducting portions 108, 110 of the sensor 100.

Figure 14:
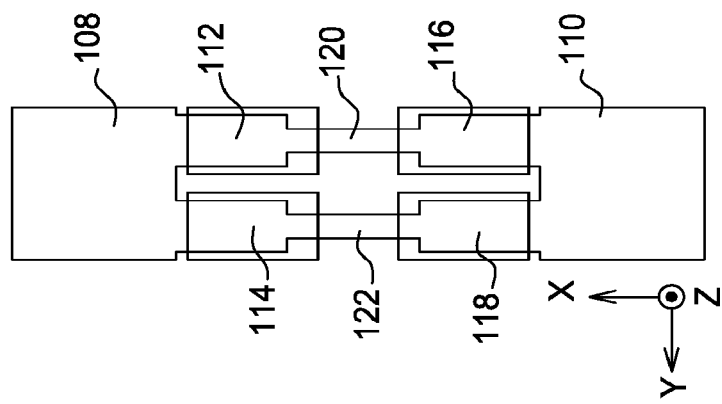

Lithography and etching are then done on the surface layer 142 to define and form the nanowires 120, 122 and the semiconducting portions 108, 110 (FIG. 14). On FIG. 14, the regions 105, 107, 109 and 111 are shown symbolically to clearly show the lithography and etching done.

When the nanowires 120, 122 comprise semiconductor doped with the same type of dopants as the regions to which the nanowires are connected, the steps described above with reference to FIGS. 12 to 14 can be replaced by those described below with reference to FIGS. 15 to 19.

Figure 15:
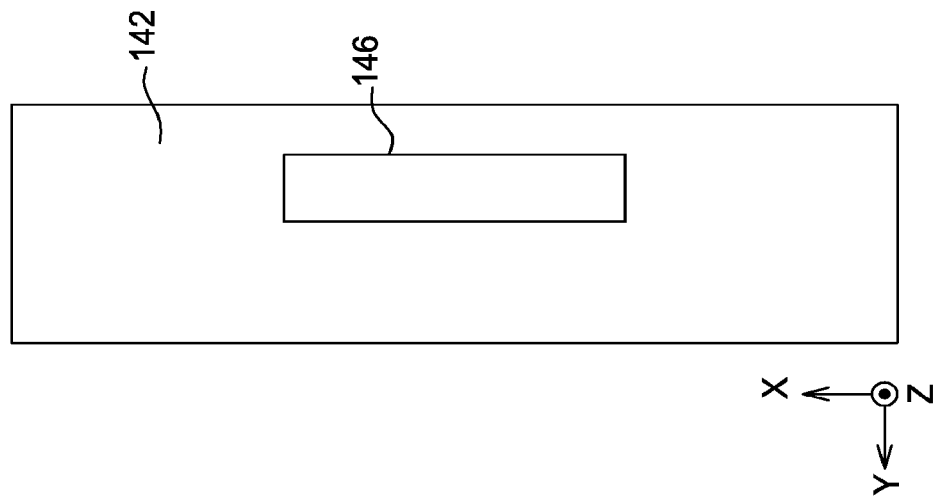

As shown on FIG. 15, a first implantation of dopants with the first type of conductivity is made in a region 146 of the layer 142 including the future first parts 112 and 116 and the first nanowire 120. The concentration of dopants implanted in the region 146 corresponds to the required concentration of dopants in the first nanowire 120.

Figure 16:
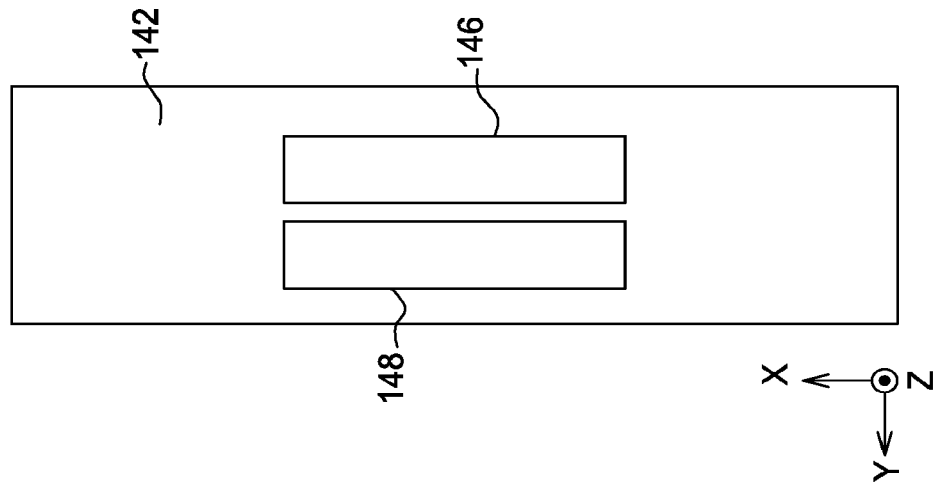

A second implantation of dopants with the second type of conductivity is made in another region 148 of the layer 142 including the future second parts 114 and 118 and the second nanowire 122 (FIG. 16). The concentration of dopants implanted in the region 148 corresponds to the required concentration of dopants in the second nanowire 122.

Figure 17:
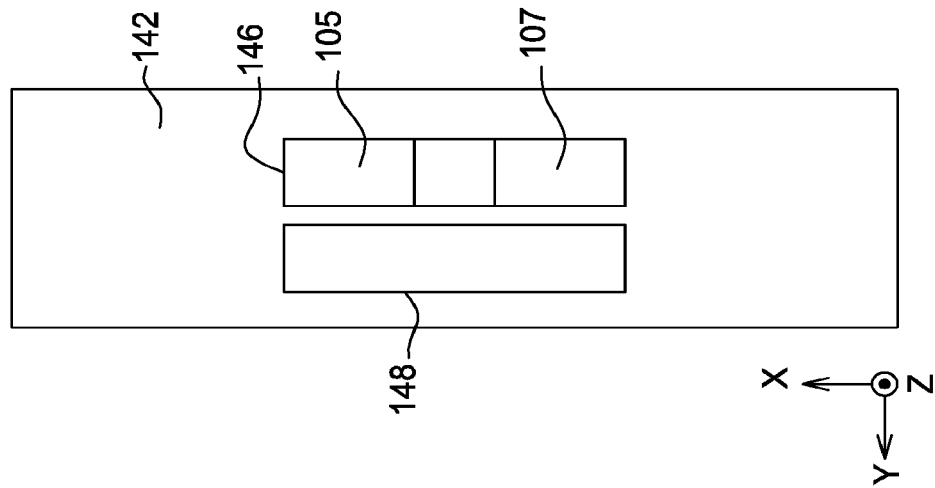

A third implantation of dopants with the first type of conductivity is made in the first regions 105 and 107 regions of the layer 142 including the future first parts 112, 116 of the first and second semiconducting portions 108, 110 of the sensor 100, and such that these first regions 105 and 107 comprise a higher doping level than the semiconducting portion that will form the first nanowire 120 (FIG. 17).

Figure 18:
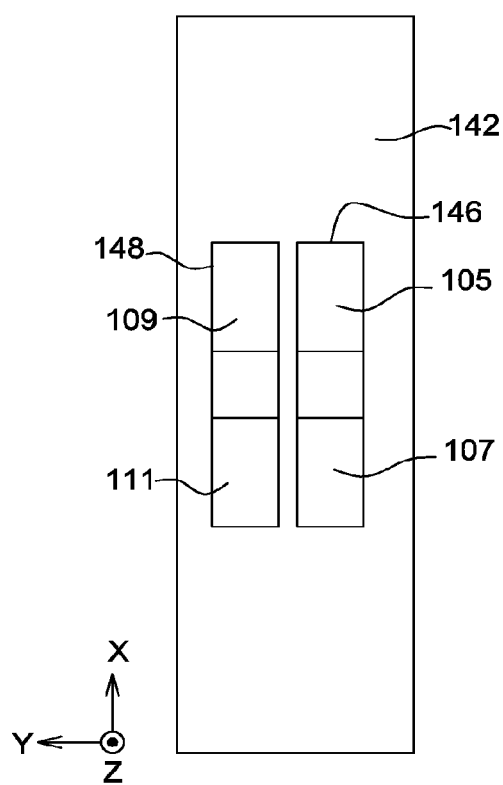

A fourth implantation of dopants with the second type of conductivity is made in the second regions 109 and 111 of the layer 142 including the future second parts 114, 118 of the first and second semiconducting portions 108, 110, and such that these second regions 109 and 111 comprise a higher doping level than the semiconducting portion that will form the second nanowire 122 (FIG. 18).

Figure 19:
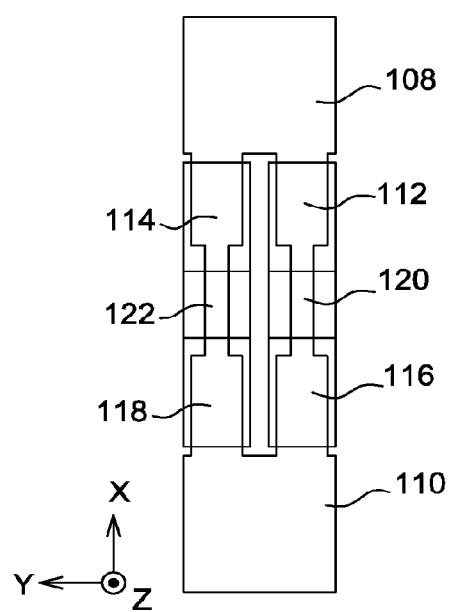

Lithography and etching are then done on the surface layer 142 to define and form the nanowires 120, 122 and the semiconducting portions 108, 110 (FIG. 19). On FIG. 19, the regions 105, 107, 109 and 111 are shown symbolically to clearly show the lithography and etching done.

As an alternative, when the nanowires 120, 122 comprise a semiconductor doped with a type different from the type of the semiconductor of the parts to which the nanowires are connected, steps similar to those described with reference to FIGS. 15 to 19 are used, however with different types of doping from the dopings done in the regions 146, 148 and the dopings made afterwards in the regions 105, 107, 109 and 111.

In all cases, implanted dopings are then activated, for example by annealing the sensor 100. This activation is applied with a heat budget compatible with the materials used.

The steps described with reference to FIGS. 12 to 19 are used collectively for all sensors 100 made on the same substrate, in other words in the same surface layer 142.

Figures 20, 21:
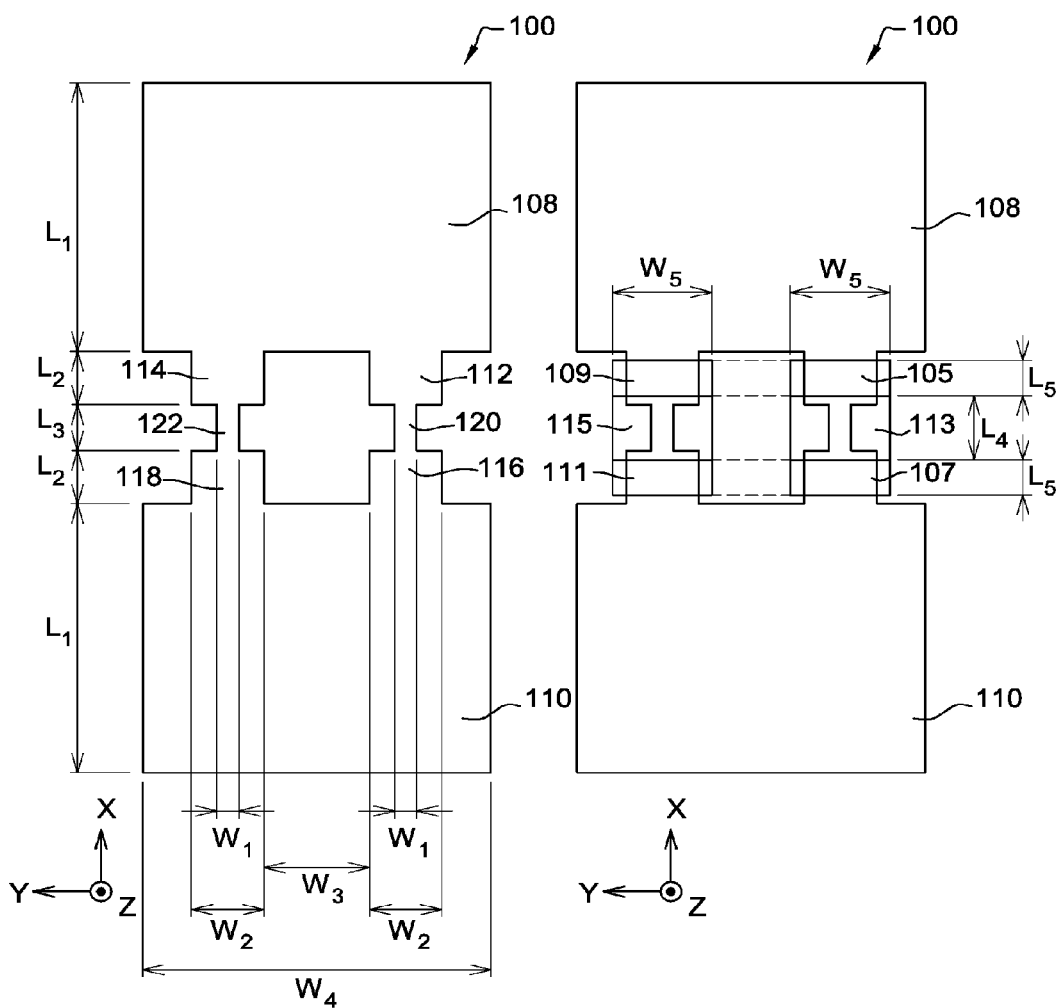

FIGS. 20 and 21 show an example geometry of the active part of the sensor 100.

Each of the semiconducting portions 108, 110 comprises a first region with a square section for which the dimensions of the sides are $L_1$ and $W_4$, for example equal to about 700 nm. The parts 112 and 114 of the portion 108 are made in second regions each with a rectangular section and located on the same side as the first region of the portion 108, and for which the dimensions of the sides are for example $L_2=120$ nm and $W_2=150$ nm. Similarly, the parts 116 and 118 of the portion 110 are made in second regions each with a rectangular section and located on the same side as the first region with a square section of the portion 110, and for which the dimensions of the sides are for example $L_2=120$ nm and $W_2=150$ nm. The first nanowire 120 is made in a third region with a rectangular section joining the second regions of the parts 112 and 116 for which the side dimensions are for example $L_3=100$ nm and $W_1=50$ nm. Similarly, the second nanowire 122 is made in a third rectangular section joining the second regions of the parts 114 and 118 for which the side dimensions are for example $L_3=100$ nm and $W_1=50$ nm.

The different dopings of the parts 112, 114, 116, 118 and possibly of the nanowires 120, 122 are applied in regions for example like those shown on FIG. 21. The regions 105, 107, 109 and 111 of parts 112, 114, 116, 118 are each for example rectangular in shape with side dimensions $W_5=200$ nm and $L_5=80$ nm. Regions 113 and 115 of the nanowires 120, 122 are each for example rectangular in shape and with side dimensions $W_5=200$ nm and $L_4=120$ nm.

FIGS. 20 et 21 clearly illustrate the fact that the different regions described above forming the first and second semiconducting nanowires 120, 122 and the first and second semiconducting portions 108, 110 are parts of the same continuous semiconducting element formed by etching in the semiconducting layer 142.

Figure 22:
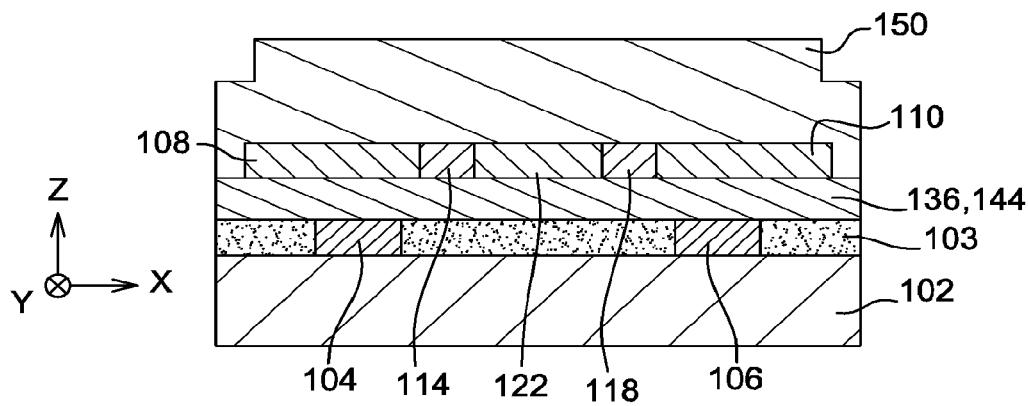

After the active part of the sensor 100 formed by the portions 108, 110 and the nanowires 120, 122 have been made, a first passivation layer 150, for example containing TEOS, is deposed on the entire structure made, in particular covering the active part of the sensor 100 (FIG. 22).

Figure 23:
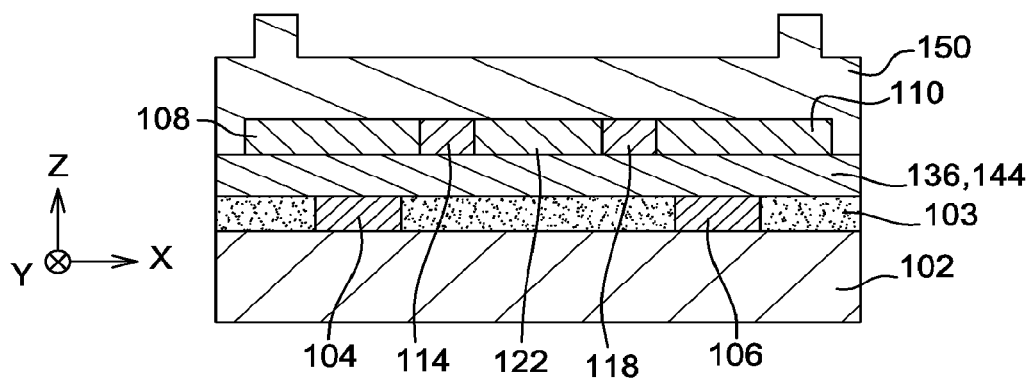

FIG. 23 shows a lithography step called a "counter mask" that includes partial etching of the dielectric (with etching depth equal to the thickness of the silicon layer) and then stripping. In defining the mask of this lithography by a negative mask dimension ZACT of −500 nm, the thickness on the dielectric layer to be removed by CMP later is reduced (step described with reference to FIG. 24). This makes the thickness of this dielectric layer more uniform.

Figure 24:
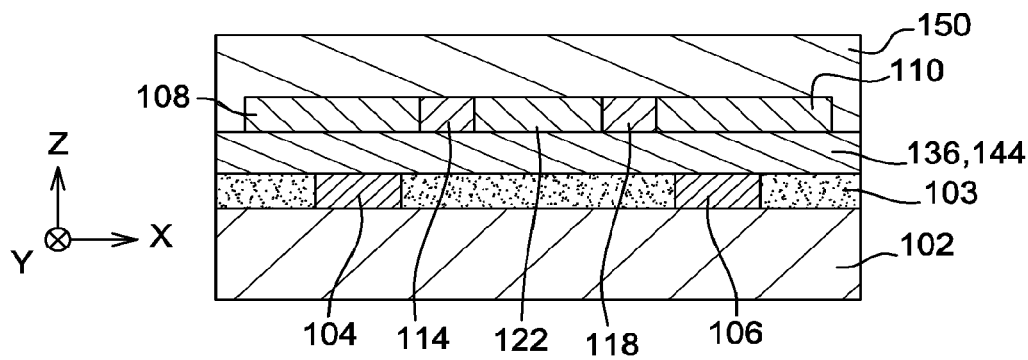

As shown on FIG. 24, CMP is then applied to polish the first passivation layer 150.

Figure 25:
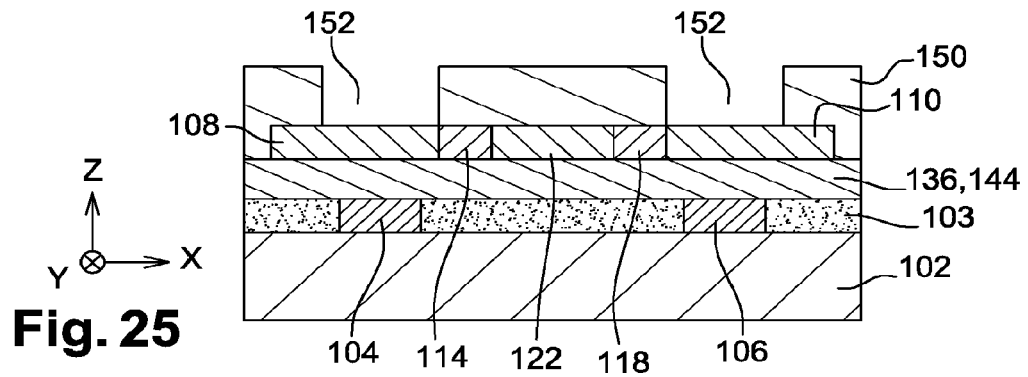
Figure 26:
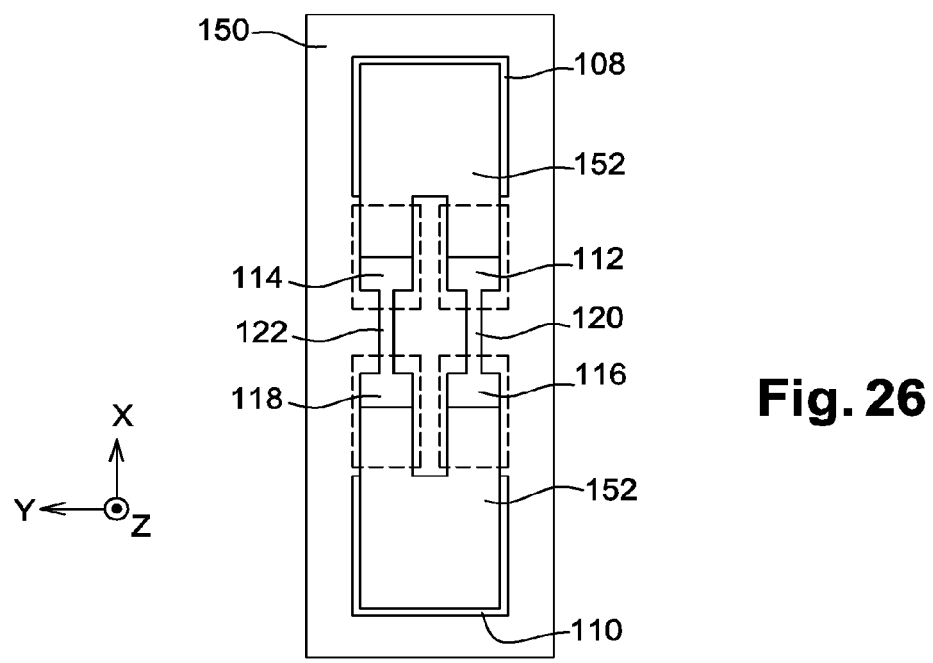

Openings 152 are then made through the first passivation layer 150 facing the portions 108, 110 so as to access these portions (FIGS. 25 and 26).

Figure 27:
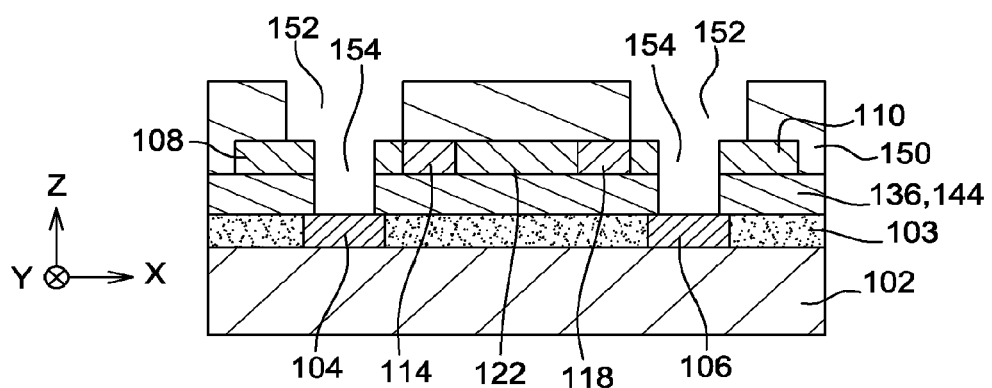
Figure 28:
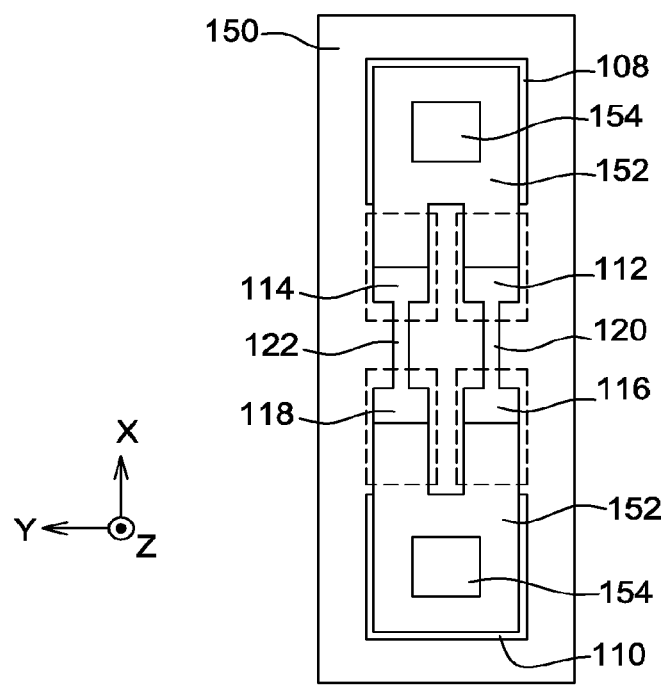

Other openings 154 are then etched through the portions 108, 110 and the bonding layers 136, 144, these openings 154 opening up onto connection pads 104, 106 (FIGS. 27, 28).

Figure 29:
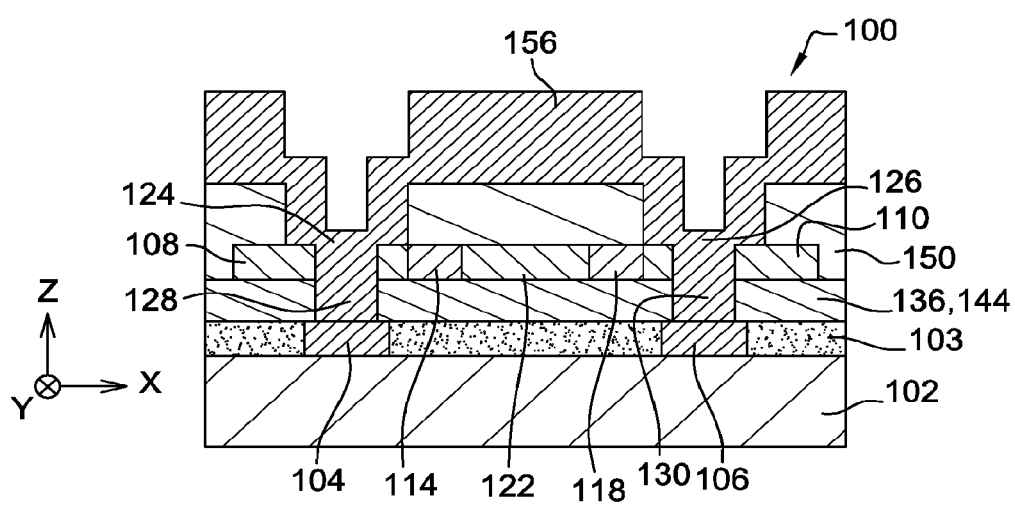

A metallic layer 156 is then deposited on the entire structure, particularly such that the openings 154 are filled with metal from layer 156, thus forming the conducting vias 128, 130 (FIG. 29). The parts of this metallic layer 156 that partially cover the portions 108, 110 form electrical contacts 124, 126.

Figure 30:
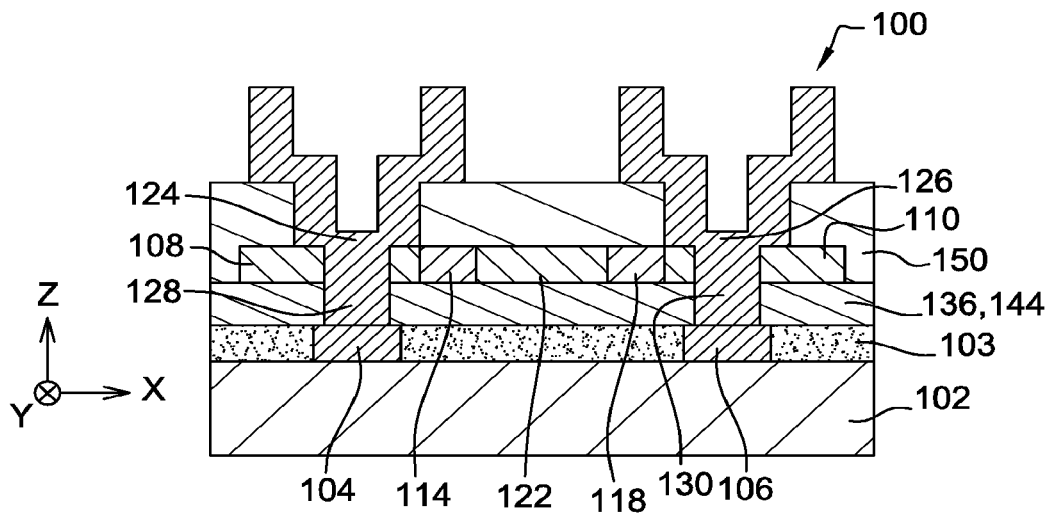
Figure 31:
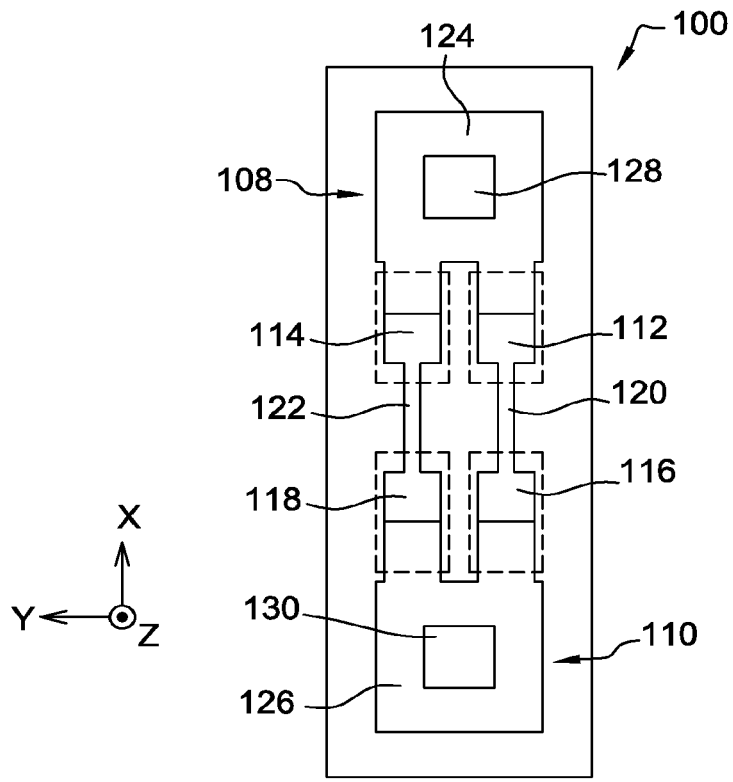

Lithography and etching of the metallic layer 156 are then used, eliminating parts of the layer 156 located on the first passivation layer 150 and that do not form part of the electrical contacts 124, 126 (FIGS. 30, 31). This etching also electrically isolates the electrical contacts 124, 126 from each other by eliminating metallic parts connecting the electrical contacts 124, 126 to each other.

Figure 32:
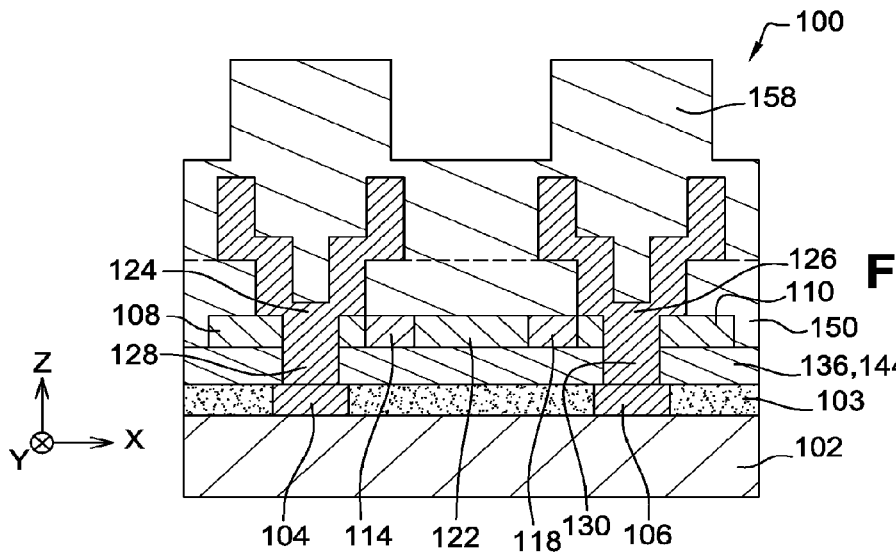

As shown on FIG. 32, a second passivation layer 158, for example containing TEOS, is deposited over the entire structure.

Figure 33:
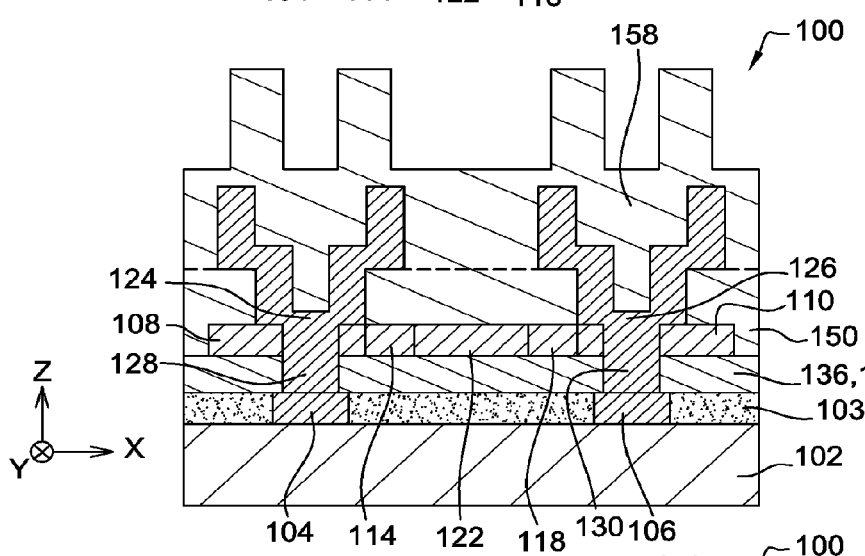

FIG. 33 shows a "countermask" lithography step followed by etching and then stripping. Dimensions are defined relative to the metal level mask.

Figure 34:
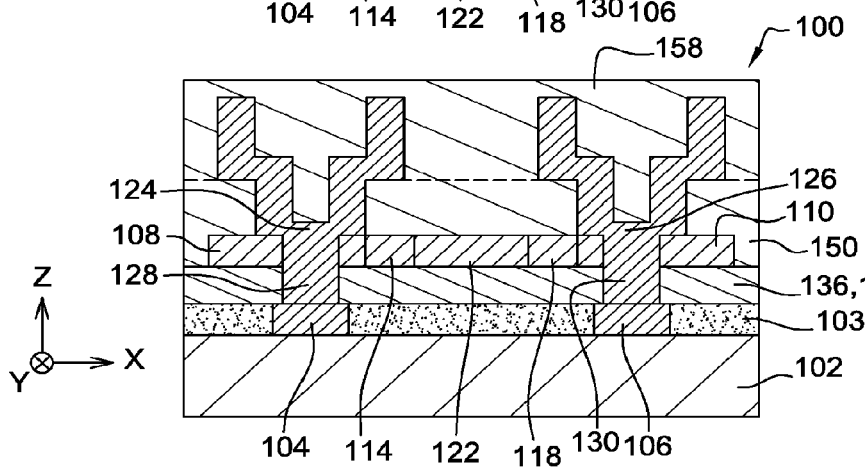
Figure 35:
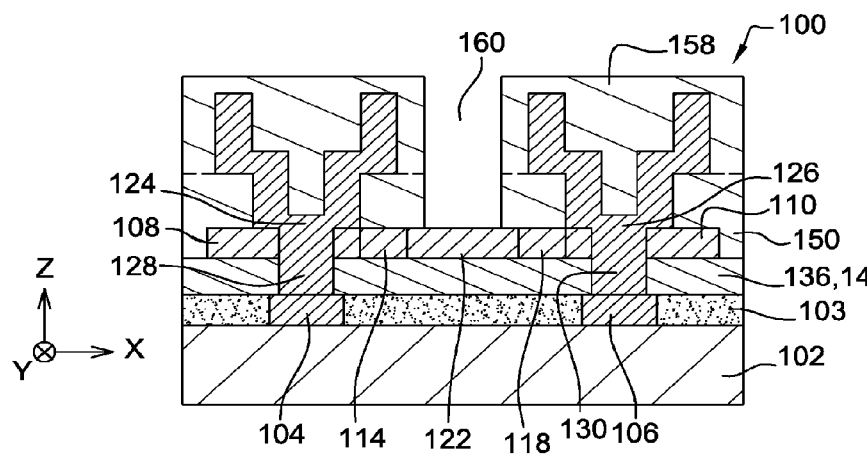
Figure 36:
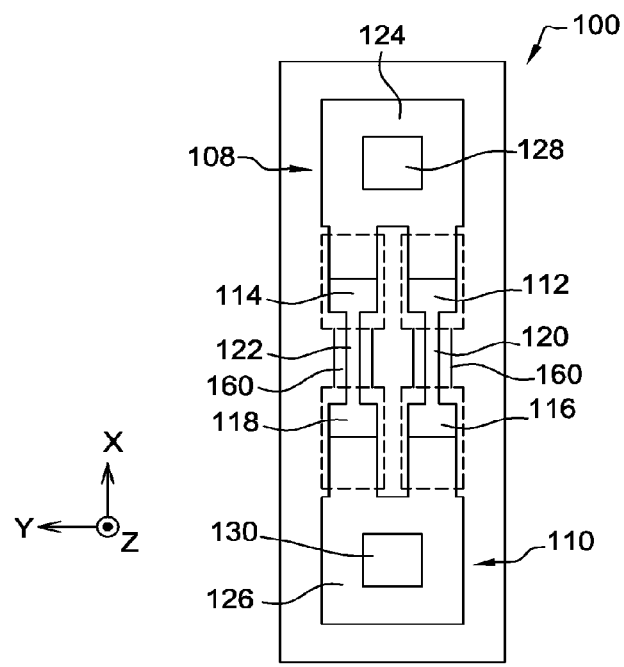

As shown on FIG. 34, CMP is then applied to polish the second passivation layer 158.

The device 100 is then completed by making an opening 160 through the passivation layers 150, 158 that form a second dielectric layer covering the semiconducting portions 108, 110 and the electrical contacts 124, 126 until the nanowires 120, 122 are reached. The opening 160 thus forms a microfluid cavity in which the fluid comprising electrically charged particles to be detected by the sensor 100 will be introduced to be in contact with the nanowires 120, 122.

The invention claimed is:

1. NW-FET sensor comprising at least:
   first and second semiconducting nanowires forming two distinct channels;
   a first semiconducting portion forming a source region, of which a first part doped with a first type of conductivity is connected to a first end of the first semiconducting nanowire, and a second part doped with a second type of conductivity opposite the first type of conductivity, is connected to a first end of the second semiconducting nanowire;
   a second semiconducting portion forming a drain region, of which a first part doped with the first type of conductivity is connected to a second end of the first semiconducting nanowire, and a second part doped with the second type of conductivity is connected to a second end of the second semiconducting nanowire;
   a first electrical contact placed on the first semiconducting portion and electrically connected to the first and second parts of the first semiconducting portion;
   a second electrical contact placed on the second semiconducting portion and electrically connected to the first and second parts of the second semiconducting portion.

2. NW-FET sensor according to claim 1, in which the first and second semiconducting nanowires and the first and second semiconducting portions are parts of a single continuous semiconducting element.

3. NW-FET sensor according to claim 1, in which the first part of the first semiconducting portion is separated from the second part of the first semiconducting portion by a distance equal to at least about 20 nm and/or the first part of the second semiconducting portion is separated from the second part of the second semiconducting portion by a distance equal to at least about 20 nm.

4. NW-FET sensor according to claim 1, in which:
the semiconductor of the first and second nanowires is intrinsic, or
the first semiconducting nanowire is doped with a first type of conductivity with a doping level less than the doping level of the first parts of the first and second semiconducting portions, and the second semiconducting nanowire is doped with a second type of conductivity with a doping level less than the doping level of the second parts of the first and second semiconducting portions, or
the first semiconducting nanowire is doped with the second type of conductivity and the second semiconducting nanowire is doped with the first type of conductivity.

5. NW-FET sensor according to claim 1, also comprising at least one first dielectric layer on which the semiconducting nanowires and the first and second semiconducting portions are placed.

6. NW-FET sensor according to claim 5, also comprising at least one gate electrode placed in the first dielectric layer, facing at least one of the first and second semiconducting nanowires.

7. NW-FET sensor according to claim 5, also comprising:
a substrate located under the first dielectric layer and comprising a CMOS control and read circuit;
electrical interconnection levels located in the first dielectric layer and electrically connected to the CMOS control and read circuit;
at least two electrically conducting vias each passing through one of the first and second semiconductor portions and a part of the first dielectric layer, and electrically connecting the first and second electrical contacts to one of the electrical interconnection levels.

8. NW-FET sensor according to claim 1, also comprising at least one second dielectric layer covering at least the first and second semiconducting portions and the first and second electrical contacts, and at least one opening passing through the second dielectric layer facing the first and second semiconducting nanowires and forming a micro-fluidic cavity of the NW-FET sensor.

9. Detection device comprising several NW-FET sensors according to claim 1, in which each of the NW-FET sensors or groups of NW-FET sensors are arranged adjacent to each other forming a detection matrix.

10. Detection device according to claim 9 in which, in each group of NW-FET sensors, one of the first and second semiconducting portions of a first of the NW-FET sensors in said group is common to at least one second of the NW-FET sensors in said group and comprises at least one third part doped with the first type of conductivity connected to one of the first and second ends of the first semiconducting nanowire of the second NWFET sensor in said group, and a fourth part doped with the second type of conductivity connected to one of the first and second ends of the second semiconducting nanowire of the second NW-FET sensor in said group.

11. Detection device according to claim 9, in which each group of NW-FET sensors comprises four first NW-FET sensors and eight second NW-FET sensors such that one of the first and the second semiconducting portions of the first NW-FET sensors is in common and the other of the first and second semiconducting portions of each is in common with two of the other second NW-FET sensors, and such that one of the first and second semiconducting portions of each of the second NW-FET sensors is in common with another of the second NW-FET sensors.

12. Method of making an NWFET sensor, comprising at least steps to:
dope first regions of a semiconducting layer with a first type of conductivity, and second regions of the semiconducting layer with a second type of conductivity opposite the first type of conductivity;
etch the semiconducting layer, forming:
first and second semiconducting nanowires forming two distinct channels of the NW-FET sensor;
a first semiconducting portion forming a source region of the NW-FET sensor, of which a first part included in one of the first doped regions is connected to a first end of the first semiconducting nanowire, and a second part included in one of the second doped regions is connected to a first end of the second semiconducting nanowire;
a second semiconducting portion forming a drain region of the NW-FET sensor, of which a first part included in another of the first doped regions is connected to a second end of the first semiconducting nanowire, and a second part included in another of the second doped regions is connected to a second end of the second semiconducting nanowire;
make a first electrical contact on the first semiconducting portion and electrically connected to the first and second parts of the first semiconducting portion;
make a second electrical contact on the second semiconducting portion and electrically connected to the first and second parts of the second semiconducting portion.

13. Method according to claim 12, also comprising steps before the doping step of the first and second regions of the semiconducting layer, to:
make a substrate comprising a CMOS control and read circuit;
make electrical interconnection levels in a first dielectric layer arranged on the substrate, the electrical interconnection levels being electrically connected to the CMOS control and read circuit;
make a semiconducting layer on the first dielectric layer.

14. Method according to claim 13, also comprising, after the step to etch the semiconducting layer, application of a step to make at least two openings each passing through one of the first and second semiconducting portions and a part of the first dielectric layer and such that they open up on one of the levels of electrical interconnections, and then a step to deposit an electrically conducting material in the two openings and on the first and the second semiconducting portions, forming the first and second electrical contacts and two electrically conducting vias each passing through one of the first and second semiconducting portions and a part of the first dielectric layer, and electrically connecting the first and second electrical contacts to said one of the electrical interconnection levels.

* * * * *